US012168001B2

United States Patent
Yi et al.

(10) Patent No.: US 12,168,001 B2
(45) Date of Patent: Dec. 17, 2024

(54) USE OF L-ERGOTHIONEINE TO AMELIORATE AND PREVENT AGE-RELATED VITREOUS DEGENERATION

(71) Applicant: NANJING NUTRABUILDING BIO-TECH CO., LTD., Nanjing (CN)

(72) Inventors: Ronghua Yi, Nanjing (CN); Qiru Fan, Nanjing (CN); Mingru Wang, Nanjing (CN); Ou Wang, Nanjing (CN); Kylin Liao, Nanjing (CN)

(73) Assignee: NANJING NUTRABUILDING BIO-TECH CO., LTD., Nanjing (CN)

( * ) Notice: Subject to any disclaimer, the term of this patent is extended or adjusted under 35 U.S.C. 154(b) by 0 days.

(21) Appl. No.: 18/391,360

(22) Filed: Dec. 20, 2023

(65) Prior Publication Data
US 2024/0122900 A1  Apr. 18, 2024

Related U.S. Application Data

(63) Continuation of application No. PCT/CN2022/100005, filed on Jun. 21, 2022.

(30) Foreign Application Priority Data

Jun. 22, 2021 (WO) ................ PCT/CN2021/101508

(51) Int. Cl.
*A61K 31/4172* (2006.01)
*A61P 27/02* (2006.01)

(52) U.S. Cl.
CPC .......... *A61K 31/4172* (2013.01); *A61P 27/02* (2018.01)

(58) Field of Classification Search
CPC .............. A61K 31/4172; A61K 9/0019; A61K 9/0095; A61K 9/08; A61P 27/02; A61P 27/10
See application file for complete search history.

(56) References Cited

U.S. PATENT DOCUMENTS

| 6,103,746 A | 8/2000 | Yarosh |
| 2008/0107603 A1* | 5/2008 | Aruoma ............... A61K 31/355 514/8.4 |
| 2010/0197750 A1 | 8/2010 | Yarosh |

FOREIGN PATENT DOCUMENTS

| CN | 114588065 A | 6/2022 |
| WO | 2007008548 A2 | 1/2007 |

OTHER PUBLICATIONS

Katarina Valachova et al., "Impact of Ergothioneine, Hercynine, and Histidine on Oxidative Degradation of Hyaluronan and Wound Healing.", Polymers, vol. 13, Dec. 29, 2020 (Dec. 29, 2020), 95 ; pp. 1-9.

(Continued)

*Primary Examiner* — Savitha M Rao
(74) *Attorney, Agent, or Firm* — ANOVA LAW GROUP, PLLC

(57) ABSTRACT

The present invention provides methods, compositions (e.g., eyedrop or spongarion composition), and uses for alleviating and preventing age-associated vitreous degeneration in a mammal, comprising administrating to the mammal in need thereof a therapeutically effective amount of L-ergothioneine, an analog or derivative thereof, or a pharmaceutically acceptable salt, acid, ester, polymer, analog or derivative thereof, as an active ingredient. In particular, L-ergothioneine is capable of scavenging chronic reactive oxygen species directly and radically to mitigate and prevent HA depolymerization and HA decreasing-viscosity in the mammal's vitreous body; and/or improving vitreous liquefaction in the mammal.

12 Claims, 1 Drawing Sheet

(56) References Cited

OTHER PUBLICATIONS

World Intellectual Property Organization (WIPO) International Search Report for PCT/CN2022/100005 Jun. 21, 2022 6 pages.
Katarina Valachova et al., "Impact of Ergothioneine, Hercynine, and Histidine on Oxidative Degradation of Hyaluronan and Wound Healing", Polymers. 2021, 13, 95; pp. 1-9. Dec. 29, 2020.

\* cited by examiner

USE OF L-ERGOTHIONEINE TO AMELIORATE AND PREVENT AGE-RELATED VITREOUS DEGENERATION

CROSS-REFERENCE TO RELATED APPLICATION

This application is a continuation application of International Patent Application No. PCT/CN2022/100005, filed on Jun. 21, 2022, which claims the priority of the International Application No. PCT/CN2021/101508, filed on Jun. 22, 2021, the contents of all of which are incorporated herein by reference in their entirety.

FIELD OF THE INVENTION

This invention generally relates to the field of methods for alleviating and preventing age-related (age-associated) vitreous degeneration in a mammal, and more specifically relates to methods comprising administrating to a mammal in need thereof: L-ergothioneine, an analog or derivative thereof, or a pharmaceutically acceptable salt, acid, ester, polymer, analog or derivative thereof, as an active ingredient, in order to alleviate and/or prevent age-related (age-associated) vitreous degeneration in the mammal.

BACKGROUND

Vitreous body is an important extracellular matrix, which is highly hydrated and relatively acellular except in the periphery where hyalocytes reside in the vitreous cortex. Vitreous consists of 98% water and macromolecules, among which the most important macromolecules are collagens and hyaluronan (HA), and organized in an exquisitely clear gel. See, e.g., Bishop, P. N., *Structural macromolecules and supramolecular organisation of the vitreous gel*. Progress in Retinal and Eye Research, 2000. 19(3): p. 323-344. Vitreous contributes to intraocular media clarity, the regulation of intraocular oxygen tension, and the maintenance of intraocular pressure.

Notably, vitreous degeneration may occur as a "normal aging" process, if molecular changes within the vitreous body arise from molecular changes within the vitreous body—which tends to occur at the vitreoretinal interface throughout life and ultimately attain sufficient prominence to alter vitreous structure. In general, vitreous degeneration is a natural phenomenon and commences quite early in life, with 12.5% of the vitreous gel being liquified by age 18 years. After increasing during growth and development, the volume of the gel remains stable until about the fifth decade when it begins to decrease in parallel with an increase in liquid vitreous. What's worse, approaches to 50% of the vitreous gel is liquified by the eighth and ninth decades. See, e.g., Ueno, N., et al., *Effects of visible-light irradiation on vitreous structure in the presence of a photosensitizer*. Experimental Eye Research, 1987. 44(6): p. 863-870. In addition to altering the internal structure of the vitreous body, aging also weakens vitreoretinal adhesion. See, e.g., Toyama, T., et al., *Posterior vitreous detachment and macular microvasculature in the elderly*. PLoS One, 2020. 15(4): p. e0231351. Accordingly, with the global aging population, the number of individuals with vitreous degeneration is increasing. Moreover, these problems may cause macular degeneration or vision loss in the elderly, which can be projected to be major public health problems.

Vitreous liquefaction, which is an entoptic phenomenon like floaters, is an important reason accounting for age-related degeneration of the vitreous body. It is a physico-chemical degenerative change which disrupts the homogeneity of the gel within the vitreous body, and is characterized by dissociation of HA from collagen, aggregation of collagen fibrils, and formation of lacunae (collagen-free spaces filled with liquid) within the vitreous body. In addition, reactive oxygen species (ROS) by light-induced is the important cause of HA dissociation, which in turn is a significant cause of age-related vitreous degeneration. More specifically, light in the present of a dye (i.e. riboflavin) and oxygen can generate ROS, like singlet oxygen, superoxide anion, hydroxyl radical and $H_2O_2$. These ROS have been shown to decrease the molecular weight of HA, induce HA depolymerization, decrease HA viscosity and gel volume of vitreous humor, consequently, liquefaction.

Further, if the vitreous degeneration becomes server, it will make the body hard to see clearly and thus interfere with quality of daily life. Often, people with vitreous degeneration are left untreated by medicines. Until recently, there have been developed two treatment approaches/options: (a) pars plana vitrectomy, i.e., the surgical removal of the patient's vitreous and its replacement by a saline solution, or (b) a noninvasive treatment of the vitreous opacities with a neodymium yttrium garnet laser (Nd: YAG). However, these pathways require complex and difficult operations, and may involve serious risks and complications. Moreover, despite the proven association between vitreous degeneration and oxidative damage, none of conventional antioxidant supplementations have been able to be used for effectively mitigating age-related vitreous degeneration, and they cannot attenuate age-related vitreous degeneration fundamentally.

L-ergothioneine is a water-soluble amino and antioxidant, found mainly in mushrooms, but also in king crab, meat from animals that have grazed on grasses containing L-ergothioneine, and other foods. L-ergothioneine cannot be synthesized by the human body (or other vertebrates), as it can only be supplemented by diet. It is a naturally occurring thiol/thione derivative of the essential amino acid histidine, and its molecular formula is $C_9H_{15}N_3O_2S$—combined with hydrogen, that sulfur at the end is what actually classifies it as a "thiol", the "—SH group", is either referred to as a thiol group or a sulfanyl group.

In view of the drawbacks of conventional methods for treating age-related vitreous degeneration, there remains a significant and urgent need for a novel strategy for alleviating and preventing the aging of vitreous body. It is particularly desired to have a substance to effectively and radically ameliorate and prevent age-associated vitreous degeneration.

SUMMARY

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

The present invention generally relates to methods for alleviating and preventing age-associated vitreous degeneration in a mammal, comprising administrating to the mammal in need thereof a therapeutically effective amount of L-ergothioneine, an analog or derivative thereof, or a pharmaceutically acceptable salt, acid, ester, polymer, analog or derivative thereof, as an active ingredient.

Particularly, L-ergothioneine is surprisingly found to be a substance with great potential and capability for effectively and fundamentally ameliorating and preventing age-associated vitreous degeneration. L-ergothioneine is concentrated in cells and tissues wherein exposed to OS frequently, such as ocular tissues, liver, bone marrow and seminal fluid. As L-ergothioneine ($C_9H_{15}N_3O_2S$) is tautomeric and exists predominantly in the thione form in neutral aqueous solutions. Moreover, L-ergothioneine with sulfhydryl group (—SH) has an extraordinarily antioxidant role via many pathways, such as inhibiting the degradation of HA by acting as a ROS scavenger. As such, L-ergothioneine is potentially beneficial to remove light-induced ROS in vitreous body directly. Then the HA depolymerization may be prevented in vitreous body, therewith the HA viscosity being improved. Accordingly, the vitreous liquefaction is further reduced. Therefore, L-ergothioneine may become a key active substance of targeted nutritional antioxidant supplementation aimed at reducing and preventing the development of age-related vitreous degeneration at root. According to this invention, it was surprisingly found that L-ergothioneine has great potentials and capability for ameliorating and preventing age-related vitreous degeneration in the elderly by scavenging light-induced ROS in vitreous body. Notably, it is believed that this invention is the first time to propose and conduct L-ergothioneine as an active ingredient to alleviate and prevent age-related vitreous degeneration One aspect of this invention relates to a method for alleviating and preventing age-associated vitreous degeneration in a mammal, comprising administrating to the mammal in need thereof a therapeutically effective amount of L-ergothioneine, an analog or derivative thereof, or a pharmaceutically acceptable salt, acid, ester, polymer, analog or derivative thereof, as an active ingredient.

In some embodiments, the age-related vitreous degeneration is related to phenomenon comprising vision-disturbing floaters, myopic, blurred vision, eye fatigue, vitreous liquefaction and/or vitreoretinal dystrophies.

In some embodiments, the age-related vitreous degeneration is characterized by dissociation of hyaluronan (HA) from collagen due to light-induced reactive oxygen species (ROS), aggregation of collagen fibrils, and/or formation of lacunae (collagen-free spaces filled with liquid) within the vitreous body.

In some embodiments, the administration of L-ergothioneine is capable of scavenging chronic reactive oxygen species directly and radically to mitigate and prevent HA depolymerization and HA decreasing-viscosity in the mammal's vitreous body.

In some embodiments, the administration of L-ergothioneine is capable of improving vitreous liquefaction in the mammal. In some embodiments, the mammal is an old mammal. In some embodiments, the mammal is a human or an animal (e.g., pet or cattle). For instance, the mammal is a human is aged 30 years or older (e.g., 40 years, 60 years, or 70 years).

In some embodiments, L-ergothioneine is administrated in a nutritional, drinking, pabulary or pharmaceutical composition in a food, drink, nutritional, or pharmaceutical field. In some further embodiments, L-ergothioneine is administrated in the form of eyedrops or spongarion.

In some embodiments, L-ergothioneine is administrated orally, by intravenous injection, by intramuscular injection, intraperitoneally or sublingually.

In some embodiments, L-ergothioneine is administrated in a form of solutions, liquid suspensions, parenteral solutions, injections, tablets, pills, granules, powder, film, (micro)capsules, aerosols, tonics, syrups, beverages, nourishments, snack bar or a food composition.

In some embodiments, L-ergothioneine is administrated by oral with a daily dose ranging from 2 to 2000 mg. The daily dose may be administrated by a single dose or multiple divided doses.

In some embodiments, L-ergothioneine is administrated at least once or multiple times a day. In some embodiments, wherein L-ergothioneine is administrated daily for at least seven days in one period.

Another aspect of the present invention provides an eyedrop or spongarion composition for alleviating and preventing age-associated vitreous degeneration in a mammal, comprising a therapeutically effective amount of L-ergothioneine, an analog or derivative thereof, or a pharmaceutically acceptable salt, acid, ester, polymer, analog or derivative thereof, as an active ingredient.

In some embodiments, L-ergothioneine is administrated with a daily dose ranging from 2 to 2000 mg.

In some embodiments, the age-related vitreous degeneration is related to phenomenon comprising vision-disturbing floaters, myopic, blurred vision, eye fatigue, vitreous liquefaction and/or vitreoretinal dystrophies.

In some embodiments, the age-related vitreous degeneration is characterized by dissociation of HA from collagen due to light-induced ROS, aggregation of collagen fibrils, and/or formation of lacunae (collagen-free spaces filled with liquid) within the vitreous body.

In some embodiments, wherein the administration of L-ergothioneine is capable of scavenging chronic reactive oxygen species directly and radically to mitigate and prevent HA depolymerization and HA decreasing-viscosity in the mammal's vitreous body.

In some embodiments, the administration of L-ergothioneine is capable of improving vitreous liquefaction in the mammal.

In a further aspect, the present invention provides a use of L-ergothioneine for preparing a composition for effectively alleviating and preventing age-associated vitreous degeneration in a mammal, wherein the composition comprises a therapeutically effective amount of L-ergothioneine, an analog or derivative thereof, or a pharmaceutically acceptable salt, acid, ester, polymer, analog or derivative thereof, as an active ingredient.

In some embodiments, L-ergothioneine is prepared in a form of solutions, liquid suspensions, parenteral solutions, injections, tablets, pills, granules, powder, film, (micro) capsules, aerosols, tonics, syrups, beverages, nourishments, snack bar or a food composition. For instance, the composition may be an eyedrop or spongarion.

In some embodiments, the composition comprises L-ergothioneine with a dose ranging from 2 to 2000 mg.

In some embodiments, L-ergothioneine in the composition is capable of scavenging chronic reactive oxygen species directly and radically to mitigate and prevent HA depolymerization and HA decreasing-viscosity in the mammal's vitreous body.

In some embodiments, L-ergothioneine in the composition is capable of improving vitreous liquefaction in the mammal.

In some embodiments, the age-related vitreous degeneration is related to phenomenon comprising vision-disturbing floaters, myopic, blurred vision, eye fatigue, vitreous liquefaction and/or vitreoretinal dystrophies.

Still in some embodiments, the age-related vitreous degeneration is characterized by dissociation of HA from collagen due to light-induced ROS, aggregation of collagen fibrils, and/or formation of lacunae (collagen-free spaces filled with liquid) within the vitreous body As used herein, the term "or" is meant to include both "and" and "or." In other words, the term "or" may also be replaced with "and/or."

As used herein, the singular forms "a," "an" and "the" are intended to include the plural forms as well, unless the context clearly indicates otherwise.

As used herein, the term "effective amount" refers to an amount that is required to improve at least one symptom of a medical condition in an individual.

DETAILED DESCRIPTION

Figure 1:
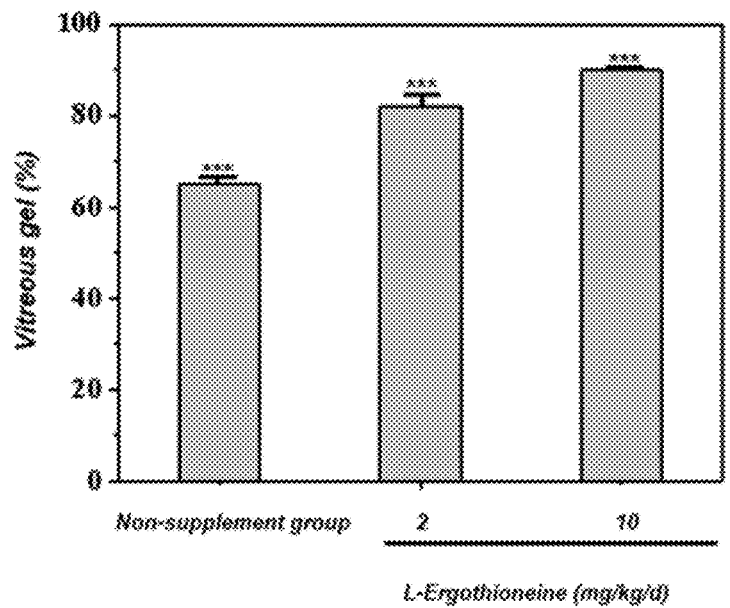
FIG. 1 exhibits the vitreous gel content (%) of the rabbits' eye (Compared with non-supplement group, ***p<0.001).

Reference will now be made in detail to the preferred embodiments of the invention, examples of which are further illustrated. While the invention will be described in conjunction with the preferred embodiments, it will be understood that they are not intended to limit the invention to these embodiments. On the contrary, the invention is intended to cover alternatives, modifications, and equivalents, which may be included within the spirit and scope of the invention as defined by the claims. Furthermore, in the detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and other features have not been described in detail as not to unnecessarily obscure aspects of the present invention.

Generally speaking, various embodiments of the present invention provide for methods for administrating L-ergothioneine (or an analog or derivative thereof, or a pharmaceutically acceptable salt, acid, ester, polymer, analog or derivative thereof) as the active ingredient to a mammal (e.g., a senior) for effectively alleviating and preventing age-associated vitreous degeneration in a mammal. For instance, the age-related vitreous degeneration may be related to phenomenon comprising vision-disturbing floaters, myopic, blurred vision, eye fatigue, vitreous liquefaction and/or vitreoretinal dystrophies. The age-related vitreous degeneration may also be characterized by dissociation of hyaluronan (HA) from collagen due to light-induced reactive oxygen species (ROS), aggregation of collagen fibrils, and/or formation of lacunae (collagen-free spaces filled with liquid) within the vitreous body. According to this invention, the administration of L-ergothioneine is capable of scavenging chronic reactive oxygen species directly and radically to mitigate and prevent HA depolymerization and HA decreasing-viscosity in the mammal's vitreous body- and/or capable of improving vitreous liquefaction in the mammal. L-ergothioneine may be administrated in a variety of forms, such as solutions, liquid suspensions, parenteral solutions, injections, tablets, pills, granules, powder, film, (micro)capsules, aerosols, tonics, syrups, beverages, and nourishments. For instance, L-ergothioneine may be administrated (e.g., by oral) with a daily dose ranging from 2 to 2000 mg for at least seven days in one period. Particularly, L-ergothioneine may be administrated in the form of eyedrops or spongarion. L-ergothioneine may be administrated with a daily dose ranging from 2 to 2000 mg, e.g., for at least seven days in one period. Additionally, the present invention provides an eyedrop or spongarion composition for alleviating and preventing age-associated vitreous degeneration in a mammal, comprising a therapeutically effective amount of L-ergothioneine, an analog or derivative thereof, or a pharmaceutically acceptable salt, acid, ester, polymer, analog or derivative thereof, as an active ingredient. Further, the present invention also provides use of L-ergothioneine for preparing a composition for effectively alleviating and preventing age-associated vitreous degeneration in a mammal, wherein the composition comprises a therapeutically effective amount of L-ergothioneine, an analog or derivative thereof, or a pharmaceutically acceptable salt, acid, ester, polymer, analog or derivative thereof, as an active ingredient.

The following examples are illustrative of select embodiments of the present invention and are not meant to limit the scope of the invention.

EXAMPLES

Fifteen young pigmented rabbits weighing 2.3-4.1 kg and aging 2.5-3 years were used in this experiment. At the onset of the investigation, each eye of every rabbit was examined by slit-lamp biomicroscopy and +60 diopter fundus lens through dilated pupils (2% atropine eye drops) to exclude any preexisting abnormalities. After slit-lamp examination, one drop of 0.5% proparacaine hydrochloride was applied for topic anesthesia, and then 0.1 mL of riboflavin ($2\times10^{-4}$ M) was injected through a Millipore filter unit into the central vitreous of both eyes, using a 30-gauge needle. All eyes were then irradiated with white light ($1.06\times10^{15}$ photons sec-1 cm-2) generated by a carousel slide projector without a lens at a distance of 60 cm for 6 hours. During irradiation, the exposed eyes were frequently treated with topical balanced salt solution (BSS) to prevent corneal drying. Their eyes were examined by using slit-lamp biomicroscopy next day, to confirm if they have serious vitreous liquefaction.

They were randomly divided into three groups: (1) non-supplement group (Con, n=5); (2) L-ergothioneine supplement group with low dosage (L-ergothioneine, 2 mg/kg/d, n=5); (3) L-ergothioneine supplement group with high dosage (L-ergothioneine, 10 mg/kg/d, n=5). Some mice were administered L-ergothioneine once daily by gavage in normal saline solution for 7 months. Their eyes were examined by using slit-lamp biomicroscopy every week, to check if their vitreous liquefaction could be improved by L-ergothioneine supplementation.

At last, these rabbits were then killed with overdose injection of sodium pentobarbital, (Anesthesia was induced by administering sodium pentobarbital (25 mg/kg) via achieve with cyclopentolate hydrochloride 1% and phenylephrine hydrochloride 10%), and the eyes were immediately removed. The vitreous body samples of rabbits were isolated from eyes radically. All tissues were frozen in optimal cutting temperature embedding compound.

Tests: Scavenge Chronic Reactive Oxygen Species to Prevent HA Depolymerization and Liquefaction The rabbits' vitreous structure could be observed by using slit-lamp biomicroscopy, to demonstrate the effect of L-ergothioneine on alleviating vitreous liquefaction.

Microscopically, the rabbits' vitreous gel were significantly increased by L-ergothioneine administration, especially in higher dose of L-ergothioneine.

Some vitreous samples of each group were poured onto a plastic resin-coated glass fiber net (mesh opening ~1.5 mm, net size 10×16 cm), which was placed on a circular filter paper. The liquefied portion of the vitreous was absorbed by the filter paper immediately, and the gel was transferred to a pre-weighed beaker (20 ml). These gel-liquid separations were done in a constant-temperature room (37° C.), and the separation time was within 30 sec. The weight of the vitreous gel was determined, and its percentage was calculated as follows: vitreous gel (%)=(separated vitreous gel wet wt (g)/initial vitreous wet wt (g))×100%.

FIG. 1 exhibits the vitreous gel content (%) of the rabbits' eye (Compared with non-supplement group, ***p<0.001). As shown, L-ergothioneine could alleviate vitreous depolymerization and liquefaction.

Antioxidant capacity of the lens was measured using an assay based on the ability of the sample to inhibit the oxidation of 2,2'-azino-di-[3-ethylbenzthiazoline sulfonate]+(ABTS) by metmyoglobin. The amount of ABTS+ produced was measured in terms of the decrease in absorbance caused by the antioxidants in the sample. Reactive oxygen species (ROS) were quantified by fluorescence spectroscopy using 2',7'-dichlorofluorescein diacetate. Testing antioxidant capacity and ROS to prove the L-ergothioneine antioxidant ability.

Figure 2:
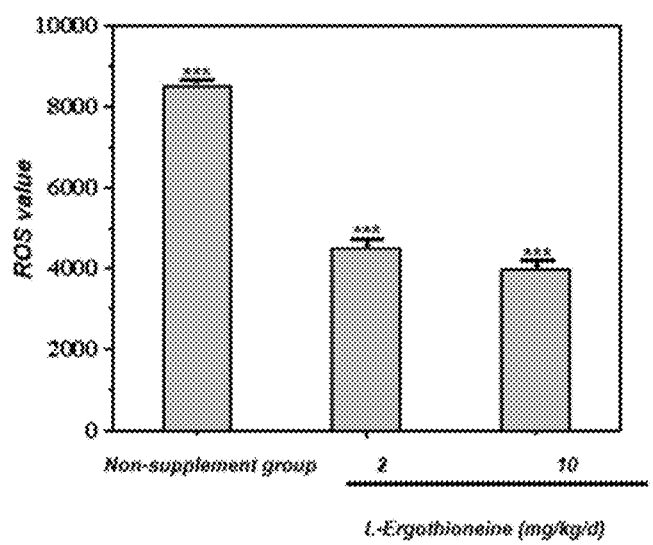
FIG. 2 is a ROS value of rabbits' lens (Compared with non-supplement group, ***p<0.001).

FIG. 2 is a ROS value of rabbits' lens (Compared with non-supplement group, ***p<0.001). As illustrated, L-ergothioneine supplementation could scavenge chronic ROS directly and radically.

Although specific embodiments and examples of this invention have been illustrated herein, it will be appreciated by those skilled in the art that any modifications and variations can be made without departing from the spirit of the invention. The examples and illustrations above are not intended to limit the scope of this invention. Any combination of embodiments of this invention, along with any obvious their extension or analogs, are within the scope of this invention. Further, it is intended that this invention encompass any arrangement, which is calculated to achieve that same purpose, and all such variations and modifications as fall within the scope of the appended claims.

All the features disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example of a generic series of equivalent or similar features.

Other Embodiments

It is to be understood that while the invention has been described in conjunction with the detailed description thereof and accompanying figures, the foregoing description and accompanying figures are only intended to illustrate, and not limit the scope of the invention, which is defined by the scope of the appended claims. Other aspects, advantages, and modifications are within the scope of the following claims. All publications referenced herein are incorporated by reference in their entireties.

What is claimed is:

1. A method for alleviating and preventing age-associated vitreous degeneration in a mammal, comprising administrating to the mammal in need thereof a therapeutically effective amount of L-ergothioneine, or an analog thereof, or a pharmaceutically acceptable salt, acid, ester, polymer, or an analog thereof, as an active ingredient, wherein L-ergothioneine is administrated in the form of eyedrops or spongarion, and the administration of L-ergothioneine is capable of scavenging chronic reactive oxygen species directly and radically to mitigate and prevent HA depolymerization and HA decreasing-viscosity in the mammal's vitreous body, resulting in an increased vitreous gel content in a mammal's eye.

2. The method of claim 1, wherein the age-related vitreous degeneration is related to phenomenon comprising vision-disturbing floaters, myopic, blurred vision, eye fatigue, vitreous liquefaction and/or vitreoretinal dystrophies.

3. The method of claim 1, wherein the age-related vitreous degeneration is characterized by dissociation of hyaluronan (HA) from collagen due to light-induced reactive oxygen species (ROS), aggregation of collagen fibrils, and/or formation of lacunae (collagen-free spaces filled with liquid) within the vitreous body.

4. The method of claim 1, wherein the administration of L-ergothioneine is capable of improving vitreous liquefaction in the mammal.

5. The method of claim 1, wherein L-ergothioneine is administrated in a nutritional, drinking, pabulary or pharmaceutical composition in a food, drink, nutritional, or pharmaceutical field.

6. The method of claim 1, wherein L-ergothioneine is administrated in a form of solutions, liquid suspensions, parenteral solutions, injections, tablets, pills, granules, powder, film, (micro) capsules, aerosols, tonics, syrups, beverages, nourishments, snack bar or a food composition.

7. The method of claim 1, wherein L-ergothioneine is administrated by oral with a daily dose ranging from 2 to 2000 mg.

8. A method of using L-ergothioneine, the method comprising preparing a composition for effectively alleviating and preventing age-associated vitreous degeneration in a mammal, wherein the composition comprises a therapeutically effective amount of L-ergothioneine, or an analog thereof, or a pharmaceutically acceptable salt, acid, ester, polymer, or an analog thereof, as an active ingredient, wherein L-ergothioneine is administrated in the form of eyedrops or spongarion, and the administration of L-ergothioneine is capable of scavenging chronic reactive oxygen species directly and radically to mitigate and prevent HA depolymerization and HA decreasing-viscosity in the mammal's vitreous body, resulting in an increased vitreous gel content in a mammal's eye.

9. The method of claim 8, wherein the composition comprises L-ergothioneine with a dose ranging from 2 to 2000 mg.

10. The method of claim 8, wherein L-ergothioneine in the composition is capable of scavenging chronic reactive oxygen species directly and radically to mitigate and prevent HA depolymerization and HA decreasing-viscosity in the mammal's vitreous body.

11. The method of claim 8, wherein L-ergothioneine in the composition is capable of improving vitreous liquefaction in the mammal.

12. The method of claim 8, wherein the age-related vitreous degeneration is related to phenomenon comprising vision-disturbing floaters, myopic, blurred vision, eye fatigue, vitreous liquefaction and/or vitreoretinal dystrophies.

* * * * *